United States Patent [19]
Fritzsch

[11] Patent Number: 5,441,499
[45] Date of Patent: Aug. 15, 1995

[54] BIPOLAR RADIO-FREQUENCY SURGICAL INSTRUMENT

[75] Inventor: Gernod Fritzsch, Tuttlingen, Germany

[73] Assignee: Dekna elektro-u. medizinische Apparatebau Gesellschaft mbH, Tuttlingen, Germany

[21] Appl. No.: 275,059

[22] Filed: Jul. 13, 1994

[30] Foreign Application Priority Data

Jul. 14, 1993 [DE] Germany .............. 43 23 585.9

[51] Int. Cl.⁶ .................................. A61B 17/39
[52] U.S. Cl. ........................ 606/45; 606/46; 604/95; 607/156
[58] Field of Search ............ 606/33, 37, 39, 41, 606/42, 45, 46, 47, 50; 607/102-103, 116, 114, 119, 154, 156; 128/4

[56] References Cited

U.S. PATENT DOCUMENTS

| | | | |
|---|---|---|---|
| 4,773,395 | 9/1988 | Suzuki et al. | 128/4 |
| 4,834,069 | 5/1989 | Umeda | 128/4 |
| 4,928,669 | 5/1990 | Sullivan | 128/4 |
| 5,007,908 | 4/1991 | Rydell . | |
| 5,192,280 | 3/1993 | Parins | 606/50 X |
| 5,220,911 | 6/1993 | Tamura | 128/4 |
| 5,314,466 | 5/1994 | Stern et al. | 607/156 |
| 5,330,470 | 7/1994 | Hagen | 606/50 X |
| 5,342,357 | 8/1994 | Nardella | 606/50 X |
| 5,360,428 | 11/1994 | Hutchinson, Jr. | 606/41 X |

FOREIGN PATENT DOCUMENTS

| | | |
|---|---|---|
| 0530400 | 3/1993 | European Pat. Off. . |
| 0544392 | 6/1993 | European Pat. Off. . |
| 2235669 | 1/1975 | France . |
| 4014350C2 | 11/1991 | Germany . |
| 4122219 | 1/1993 | Germany . |
| 9216838 U | 4/1993 | Germany . |
| 4136861 | 5/1993 | Germany . |

*Primary Examiner*—Peter A. Aschenbrenner
*Attorney, Agent, or Firm*—Townsend and Townsend Khourie and Crew

[57] ABSTRACT

The invention relates to a bipolar radio-frequency surgical instrument with a rigid tube shaft (11) and a working tip (12) which preferably has substantially the same cross-section as the adjoining part of the tube shaft (11) and is preferably centrally provided with at least one working electrode, such as a cutting electrode (13, 13") or a coagulating electrode (13') which can be energized with a radio-frequency voltage, and a neutral electrode (14) which preferably has a significantly larger surface. The working tip (12) is connected with the rigid tube shaft (11) near the distal end of the instrument in a hinged or flexible manner in such a way that the working tip (12) can be pivoted from a position which is axially aligned with the tube shaft (11) to a position which forms an angle relative to the tube shaft (11), and such that means (17, 18, 19) are provided to pivot and return the working tip (12).

13 Claims, 6 Drawing Sheets

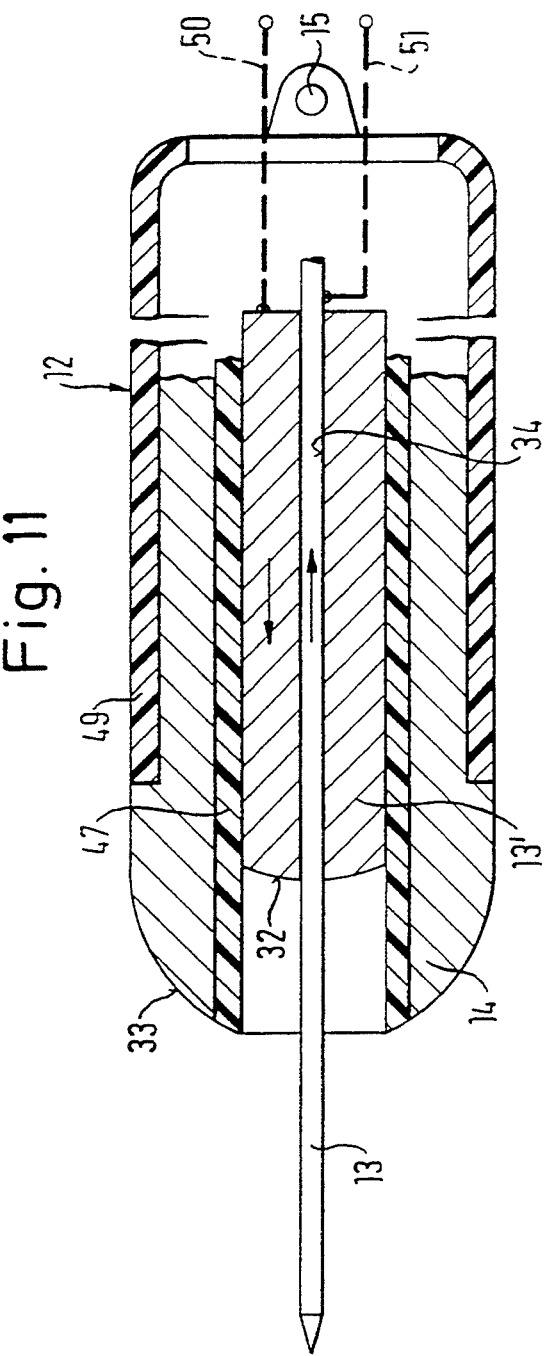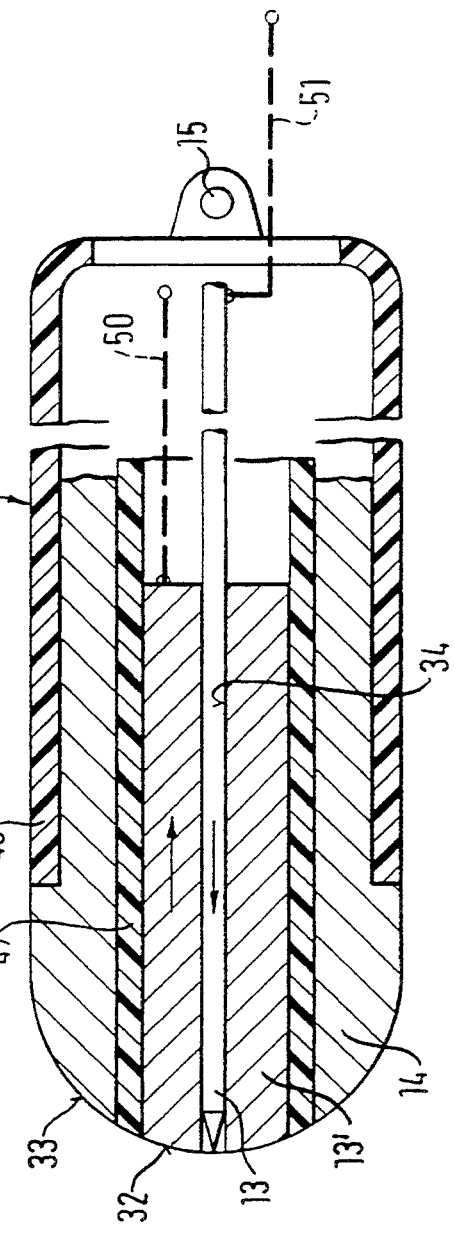

BIPOLAR RADIO-FREQUENCY SURGICAL INSTRUMENT

BACKGROUND OF THE INVENTION

The invention relates to a bipolar radio-frequency surgical instrument.

Such bipolar radio-frequency surgical instruments normally have a rigid shaft on whose distal end a neutral electrode, cutting electrode and/or coagulating electrode which is insulated relative to the neutral electrode are provided. A problem during the handling of such instruments lies in the fact that the operator can view the cutting process or coagulating process only with difficulty, particularly when the instrument is guided to the site of the operation together with a viewing endoscope through a trocar. The viewing direction of the operator is then approximately the same as the direction of the axis of the tube shaft of the surgical instrument, so that the position where the cutting electrode or coagulating electrode comes into contact with the tissue which is to be treated can only be viewed with difficulty or not at all.

For this reason, the cutting wire at the distal end of the working tip has in the past been bent far enough to the side so that it projects somewhat over the outer perimeter of the tube shaft and thus becomes viewable when the operator looks in approximately the axial direction. This arrangement however has the disadvantage that the insertion of the instrument into the trocar and the guiding to the site of the operation is made more difficult by the laterally projecting cutting electrode, and thus that the sensitive cutting electrode can be damaged therein.

A corresponding arrangement of a coagulating electrode pair has not become known hitherto.

SUMMARY OF THE INVENTION

It is an object of the invention to provide a bipolar radio-frequency surgical instrument of the initially named kind which is suitable in particular for laparoscopic surgery, i.e. which is insertable through a trocar to the site of the operation without any problems, while at the same time allowing a perfect view of the coagulating process or cutting process for the operator even in the case of an approximately axial direction of the view.

To achieve this, a bipolar radio-frequency surgical instrument is provided with a rigid tube shaft and a working tip which preferably has substantially the same cross-section as the adjoining part of the tube shaft and is preferably centrally provided with at least one working electrode, such as a cutting electrode or a coagulating electrode which can be energized with a radio-frequency voltage, and a neutral electrode which preferably has a significantly larger surface. The working tip is connected with the rigid tube shaft near the distal end of the instrument in a hinged or flexible manner in such a way that the working tip can be pivoted from a position which is axially aligned with the tube shaft to a position which forms an angle relative to the tube shaft. Means is further provided to pivot and return the working tip.

Thus, in accordance with the invention the instrument can be used alternatively with the working tip which is axially aligned with the tube shaft or bent from the tube shaft. During the insertion or extraction through a trocar, the working tip is aligned with the tube shaft in accordance with the invention, so that there are no laterally projecting parts at the distal end which inhibit the movement of the instrument within the trocar or in the body of the person being operated upon. The working tip can then be pivoted in the region of the site of the operation so that it enters the viewing range of, for example, an operator viewing the operation through an endoscope. It is known to form the distal end of endoscopes (DE 39 05 455 C2; EP 0 422 842 A2) or of catheters (EP 0 489 937 A1) in a manner which is controllably bent in order to reach regions within the body that could not be reached by a straight-lined instrument. The meaning and the purpose of the present invention, however, is not to reach normally inaccessible regions within the human body with the surgical instrument, but instead to be able to view the operating procedure immediately through an endoscope. For this, it is important that the axis of rotation of the working tip is not disposed too far away from the distal end of the instrument. In other words, if the outwardly pivoted working tip is in the cutting position or the coagulating position, then the cutting electrode or coagulating electrode should project radially over the outer perimeter of the rigid tube shaft only far enough to allow the direct viewing of the operating procedure and the electrode by the operator via an endoscope which has also been inserted through the trocar, or via a trocar which may itself be formed as an endoscope.

The preferred distances of the axis of rotation from the distal end of the instrument are such that the axis of rotation between the tube shaft and the working tip is disposed less; than 10 cm and preferably less than 5 cm, and in particular 2 to 3 cm away from the front end of the working electrode.

Three particularly preferred pivotal arrangements of the working tip are that the working tip is attached to the rigid tube shaft by means of a hinge, that a quasi-flexible section between the rigid tube shaft and the working tip is formed by several tubular hinge members, and that at least one flexural spring element is provided between the tube shaft and the working tip.

Advantageous further features of the above described embodiment are that the flexural spring element or flexural spring elements are provided eccentrically to the axis of the tube shaft, that the section modulus of the flexural spring element or of the flexural spring elements is at least three times as large in the plane of bending as in the plane perpendicular thereto, and that the flexural spring element or the flexural spring elements is or are formed as a leaf spring or as leaf springs whose flat side faces towards the central longitudinal axis of the tube shaft.

In order to adjust the working tip from its rest position disposed axially in the direction of the tube shaft to the deployment position which is angled from the tube shaft, several mechanisms are described with the means to pivot and reset the working tip comprising:
- two eccentrically arranged, oppositely disposed draw wires or
- a resetting or deployment spring arranged eccentrically to the axis of pivoting and a diametrically oppositely disposed draw member or
- a symmetrically arranged coil spring and a draw member or
- a connecting element of resilient material between the tube shaft and the working tip, and a draw member or
- a thrust and draw rod, or a control member which is axially displaceable within the tube shaft and which supports the working tip pivotally and in a deployable manner relative to the tube shaft.

The means for pivoting and returning the working tip 12 is preferably provided with abutments in such a way that the working tip can be in only two positions, in particular the rest position axially disposed in the direction of the rigid tube shaft or the deployed working position.

An additional advantageous means for adjustment of the working tip is characterized by a hinge being arranged between the working tip and the rigid tube shaft which is cut off at an angle at its distal face end at least up to the center axis, by a second tube with an inclined end face being arranged rotatably and concentrically to the rigid tube shaft, and by a draw wire preferably prestressed by a tension spring or a pressure rod prestressed by a tension spring or compression spring contacting the working tip in such a manner that a torque directed towards the inclined surface of the tube shaft is applied to the working tip.

An additional advantageous object is that the spring element is prestressed in the deployment direction, and the working tip is hinged to a control member which is axially displaceable within the tube shaft.

The spring element is preferably made of spring steel, spring bronze, or super-elastic Ni—Ti-alloy.

In a preferred embodiment the working electrode is formed as a bipolar cutting loop for the removal of biological tissue and the cutting loop is bent to the side. The metallic shaft is isolated from the loop and formed as a large-area neutral electrode whose surface is preferably at least five times as large as the surface of the cutting loop. This an advantageous means for the removal of biological tissue. For a cutting instrument, the working tip is preferably formed as a bipolar cutting needle immediately behind of which a surrounding large-area neutral electrode is provided.

The invention is preferably used with the working tip being formed as a combined bipolar cutting element and coagulating element in the case of a combined instrument which is formed such that there are coagulating electrodes and neutral electrodes which are disposed mutually concentric to and insulated from one another and whose convexly curved end faces form a uniform surface. The coagulating electrode is retractable within the tubularly designed neutral electrode, and a cutting needle can be pushed outwardly through an axial bore within the coagulating electrode.

Appropriate materials for the cutting needle comprise tungsten wire, spring steel wire, or Ni—Ti-alloy.

Particularly advantageous pivotal angles of the working tip in the working position are such that the working tip forms an angle of at least 20°, of preferably 30° to 45°, and in particular of approximately 35° with the axis of the rigid tube shaft in the working position.

BRIEF DESCRIPTION OF THE DRAWINGS

FIGS. 11, 11a are sectioned side views of a further working tip for a radio-frequency surgical instrument in accordance with the invention which allows the coagulation as well as the cutting, wherein the cutting position is illustrated in FIG. 11 and the coagulating position is illustrated in FIG. 11a.

DESCRIPTION OF THE PREFERRED EMBODIMENTS

Figure 1:
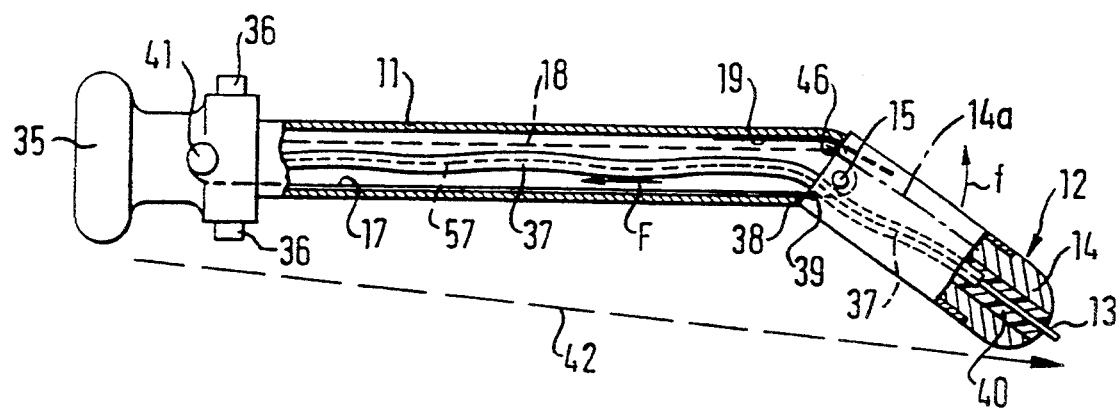
FIG. 1 is a schematic partial side view of a first embodiment of a radio-frequency surgical Cutting instrument constructed in accordance with the invention.

According to FIG. 1, the radio-frequency surgical cutting instrument of the present invention preferably has a metal and grounded rigid tube shaft 11, which at its rear end has a schematically indicated handle 35 with the actuating elements 36, 41 for the different functions and which accepts an insulated radio-frequency lead 37 within its interior, which supplies a radio-frequency voltage from a radio-frequency generator (not shown) to a cutting electrode 13 at the distal end of the instrument.

At the distal end of the preferably circularly cylindrical tube shaft 11, a working tip 12 which is preferably not longer than 2 to 3 cm is mounted on an axis of rotation 15 which extends transversely to the tube shaft axis. The pivotal range of the working tip 12 is limited to an angle of approximately 30° from the longitudinal central axis of the linear tube shaft 11 by a pair of abutment surfaces 38.

A longitudinal spring 19 extends above the axis of rotation 15 from the distal end region of the tube shaft 11 into the likewise preferably tubular working tip 12, with the spring prestressing the working tip 12 relative to the tube shaft in the direction of the arrow f in such a way that the working tip is normally aligned with the tube shaft 11 in an insertion position and withdrawal position.

A draw cable or draw wire 17 extends between a point 39 beneath the axis of rotation 15 and a turning knob 41 at the proximal end of the tube shaft 11, and can be acted on by a tensile force in the direction of the arrow F to pivot the working tip 12 against the force of the spring 19 into the working position which is evident from FIG. 1.

The insulated radio-frequency lead 37 extends past the axis of rotation 15 into the tubular working tip 12 which at its distal end has a convexly curved neutral electrode 14, within which there is an insulation core 40 surrounding the coaxially a forwardly projecting cutting electrode 13. The cutting electrode 13 is connected in an electrically conductive manner to the core assembly 57 of the radio-frequency lead 37. The with the core assembly 57 is indicated by a broken line.

The manner of operation of the radio-frequency surgical instrument which is shown in FIG. 1 is as follows:

First, the stressed draw cable 17 is loosened through a suitable actuation of the rotary knob 41 in such a way that the spring 19 can pivot the working tip 12 in the direction of the arrow f into the insertion and withdrawal position aligned with the tube shaft 11. In this position, the instrument is for example inserted through a trocar into a body cavity in which the operation is to be performed. As soon as the working tip 12 is at the site of the operation, the operator actuates the rotary knob 41, which causes the draw cable 17 to be moved in the direction of the arrow F and thus pivots the working tip 12 against the force of the spring 19 into the working position which can be seen in FIG. 1. Now the cutting electrode 13 which projects from the working tip 12 is in the operator's viewing direction which is schematically indicated at 42, so that the operation can proceed with an unhindered operator's view after the radio-frequency current is switched on via one of the actuation knobs 36 provided for this purpose. The viewing of the operating procedure then occurs through an endoscope which can extend along the viewing direction 42.

Instead of the spring 19, an additional draw wire 18 can be provided at the side which diametrically opposes the draw wire 17, with the additional draw wire 18 being attached at 46 diametrically opposite of the point of attachment 39 at the rear end of the working tip 12. By means of applying opposing tensions on the draw wires 17, 18, the working tip 12 can be pivoted to and fro between the insertion position and the withdrawal position on the one hand, and the working position on the other hand.

In the following figures,, the same reference numerals are used for components having counterparts in FIG. 1. The radio-frequency lead 37 is partly not shown for reasons of clear illustrations, however it is always present.

Figure 2:
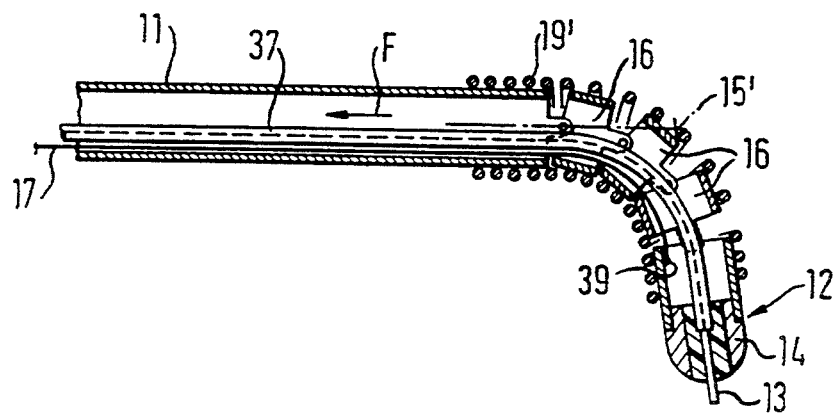
FIG. 2 is a similar view of another embodiment of the invention.

In the embodiment of FIG. 2, several hinged members 16 which are mounted in series are provided between the rigid tube shaft 11 and the working tip 12, whereby the working tip 12 can attain an especially large pivotal angle of approximately 90° about an imaginary axis of rotation 15'.

A coil spring 19' extends between and is frictionally inserted over the distal end of the tube shaft 11 and the working tip 12, with the coil spring 19' biasing the working tip 12 and the hinged members 16 in a position which is axially aligned with the tube shaft 11. By means of the draw wire 17 which is attached at 39 at a distance from the central axis, the working tip 12 can be pivoted into the working position which is evident from FIG. 2.

Figure 3:
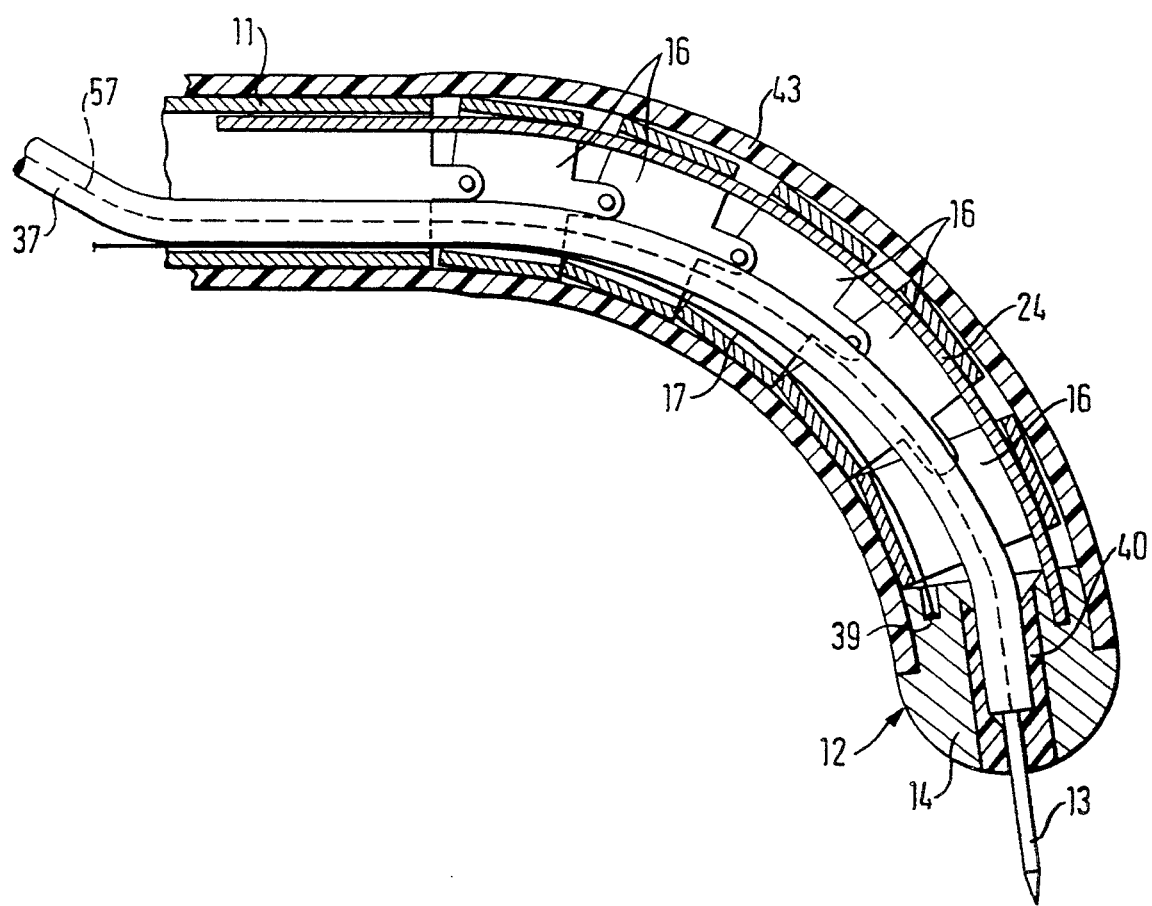
FIG. 3 is an enlarged partial side view of a similar embodiment to that of FIG. 2.

In the embodiment of FIG. 3, a flexible tube 43 of FIG. 2 is pulled over the working tip 12, the hinged members 16 and the distal end of the tube shaft 11, instead of the coil spring 19', whereby the hinged members 16 are hermetically completely closed off from the outside. The resetting spring force which is necessary for the axial alignment of the working tip 12 with the tube shaft 11 could principally be made by a suitably elastically formed insulation hose. However, in the example of the embodiment of FIG. 3, a leaf spring 24 extends between the distal end of the tube shaft 11 and the tubular neutral electrode 40 of the working tip 12 for this purpose. This leaf spring 24, together with the draw wire 17, takes care of the deployment into the working position which is evident from FIG. 3 or of the returning of the tube shaft 11 and of the working tip 12 into the axially aligned position.

Figure 4:
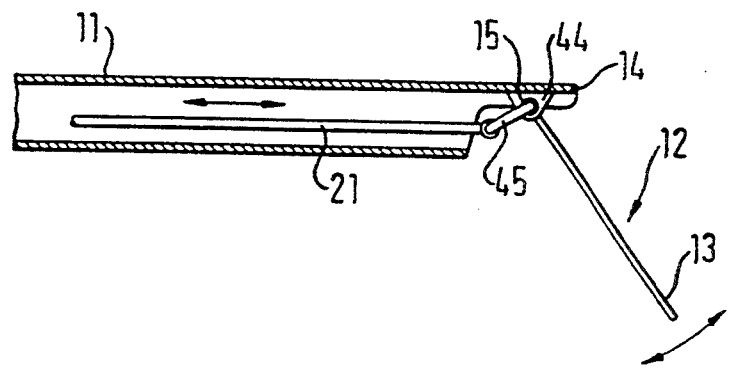
FIG. 4 is a view similar to FIGS. 1 and 2 of a further embodiment of the invention.

FIG. 4 shows a particularly simple embodiment, in which the working tip 12 is reduced to a correspondingly rigidly formed cutting needle 13, which is attached in a hinged manner at the distal end of the tube shaft 11 by means of an insulated bearing pedestal 44, i.e. is pivotally attached about an axis of rotation 15. The cutting needle 13 can be pivoted into the angled working position which is evident from FIG. 4, as well as into a position which is axially aligned with the tube shaft 11 via an angle lever 45 and a thrust rod 21 which axially extends within the tube shaft 11, wherein the thrust rod 21 can be moved in a back and forth manner and, together with the angle lever 45, forms the radio-frequency supply.

Figure 5:
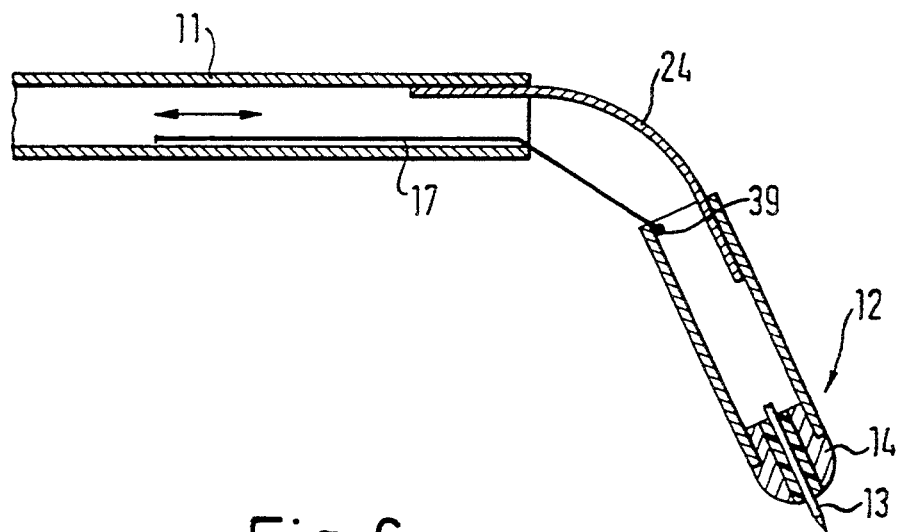
FIG. 5 is a schematic side view of a further embodiment.

FIG. 5 indicates that a flexible leaf spring 24 which extends between the tube shaft 11 and the working tip 12 can not only assume the resetting force generation between these two elements, but also provides the hinged connection of the tube shaft 11 and the working tip 12. A special mechanical hinge can thus be avoided.

Figure 6:
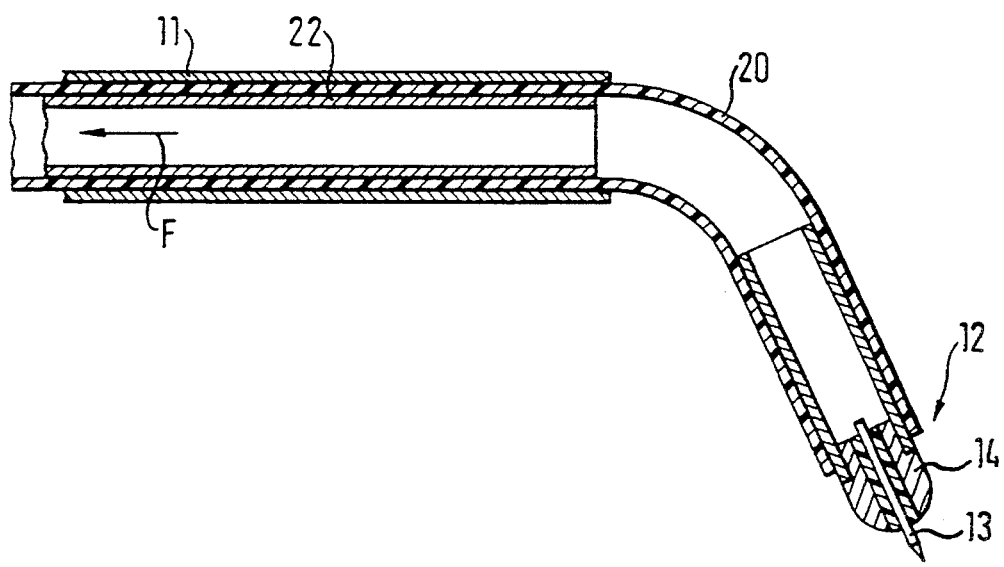
FIG. 6 is a schematic side view of an embodiment provided with an axially displaceable control member.

According to FIG. 6, an inner tube 22 which acts as a controlling element is arranged in an axially moveable manner within the tube shaft 11. The inner tube 22 is sleeved by a flexible and elastic insulation hose 20 which projects beyond the distal end of the tube 22 and of the tube shaft 11, and which from there both extends over and holds the working tip 12. In its relaxed state, the insulation hose 20 assumes the working position which is angled by approximately 60° relative to the tube shaft 11 and is shown in FIG. 6. By pulling back the tube 22 in the direction of the arrow F within the tube shaft 11, the initially curved part of the insulation hose 20 is pulled into the straight tube shaft 11 and is thus resiliently straightened. As soon as the rear end of the working tip 12 is in the distal region of the tube shaft 11, the tube shaft 11 and the working tip 12 are axially aligned and thus assume their insertion position and withdrawal position.

Figure 7:
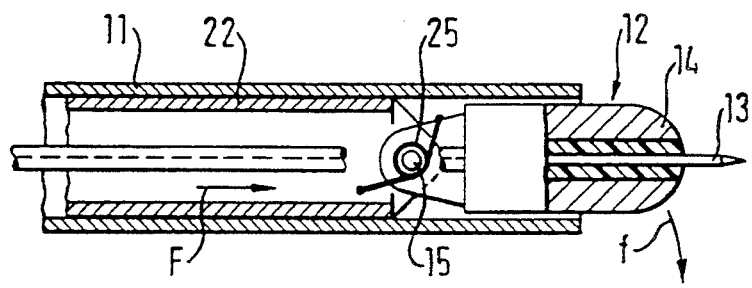
FIG. 7 is a schematic side view of an embodiment similar to that of FIG. 6, FIGS. 8, 8a show an embodiment using a rotatable selection tube in the rest or working position.

As shown in FIG. 7, the inner tube 22 which is concentric to the tube shaft 11 and acts as a control element is arranged without the sleeved insulation hose in an axially moveable manner within the tube shaft 11. A working tip 12 is attached at its front end via a hinge 15. A legged spring 25 biases the working tip 12 into the direction of the arrow f.

When the tube 22 is in the position, as evident from FIG. 7, furthest pulled back within the tube shaft 11, the correspondingly dimensioned working tip 12 is arranged with its rear end in the front portion of the tube shaft 11 and axially aligned with it.

When the inner tube 22 is now forwardly displaced in the direction of the arrow F, the working tip 12 emerges more and more from the front end of the tube shaft 11 until it completely projects from it. Now the correspondingly prestressed legged spring 25 downwardly deploys the working tip 12 in the direction of the arrow f against an abutment, so that the working tip 12 finally assumes its working position.

Figure 8:
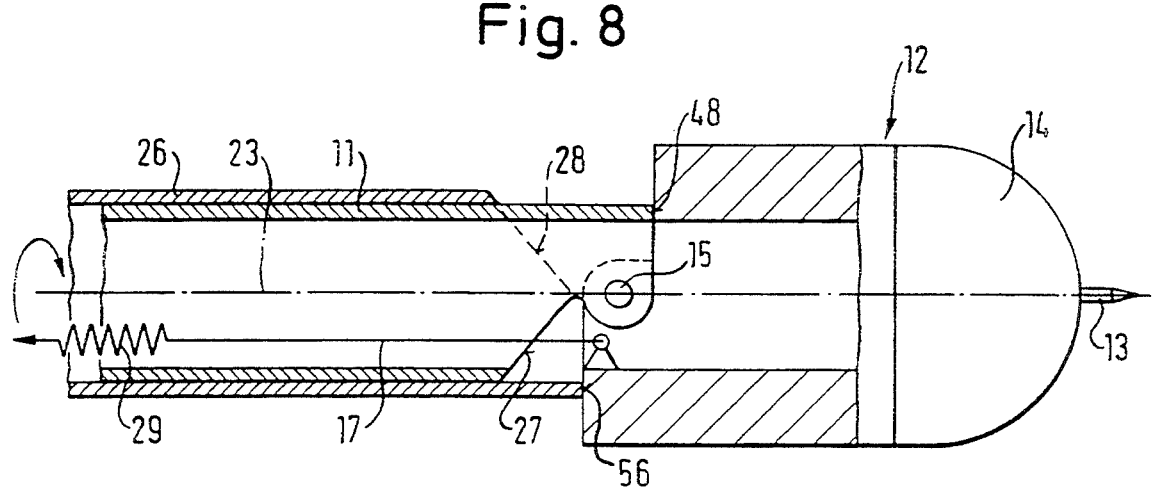

As shown in FIG. 8, a rigid tube 26 is rotatably arranged at the outside of the tube shaft 11, but not in an axially moveable manner. The front end face of the rigid tube 26 which is partly formed as an abutment surface 46 is inclined to the central longitudinal axis 23 at an angle of approximately 45° and forms an inclined surface 28 there.

The front end face surface of the rigid tube shaft 11, which is partly formed as an abutment surface 48, also has a corresponding inclination 28, which however in the rotary position of FIG. 8 is at the side of the central longitudinal axis 23 which lies diametrically opposite of the inclination of the end face surface 28.

If the two inclinations 27, 28 are offset to one another by 180° relative to the central longitudinal axis 23 of FIG. 8, a draw wire 17 which is acted on by a tension spring 29 causes the contact of the working tip 12 which is axially aligned with the tube shaft 11 against an abutment surface 46 at the front end of the rigid tube 26.

Figure 8A:
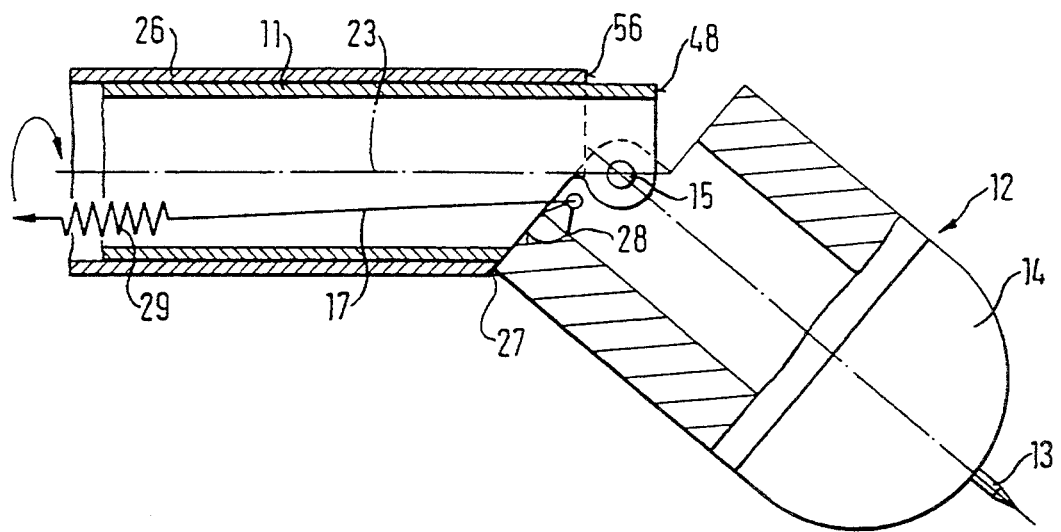

When the rigid tube 26 is now rotated by 180° relative to the central longitudinal axis 23 into the position of FIG. 8a, the inclined surface 28 instead of the abutment surface 46 provided in FIG. 8 is aligned with the inclination 27 of the tube shaft 11, whereby the working tip 12 which is acted on by the tension spring 29 via the draw wire 17 can pivotally deploy into the lower working position which can be seen in FIG. 8a, where the working tip 12 contacts the aligned inclined surfaces 27, 28.

Figure 9:
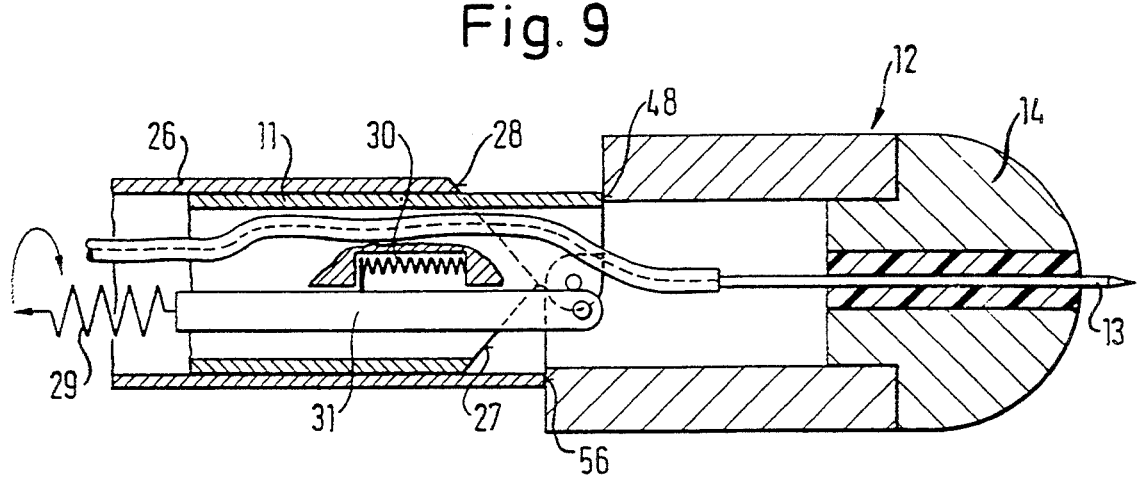
FIGS. 9, 9a show an embodiment similar to that of FIGS. 8, 8a in the rest or working position.
Figure 9A:
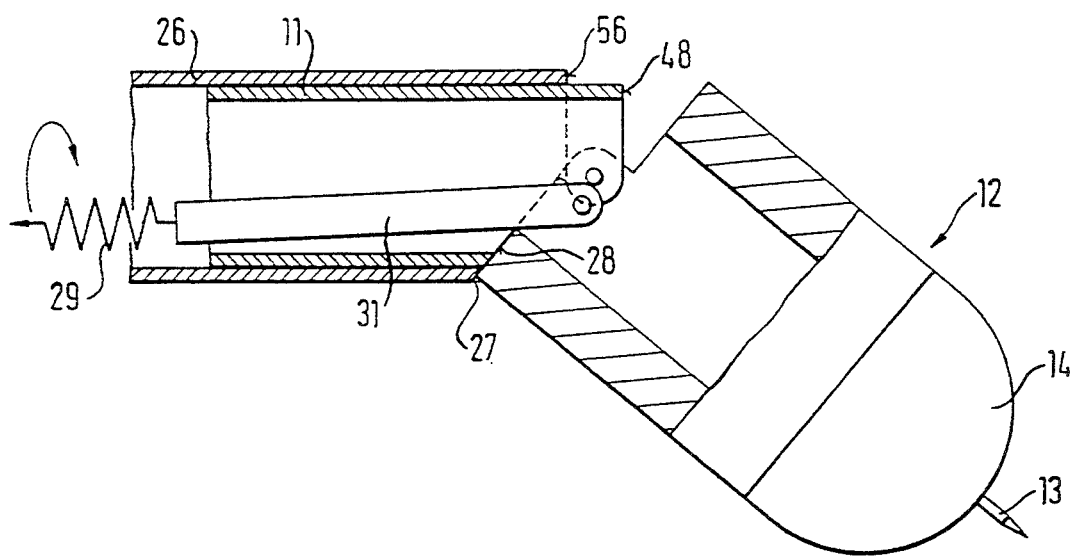

A similar embodiment is shown in FIG. 9 and FIG. 9a, wherein simply a thrust rod 31 is provided instead of the draw wire 17 in FIG. 8 and FIG. 8a. Instead of being acted on by the tension spring 29, the thrust rod 31 can be acted on by a thrust spring 30 which is indicated only in a schematic manner in FIG. 9.

Figure 10:
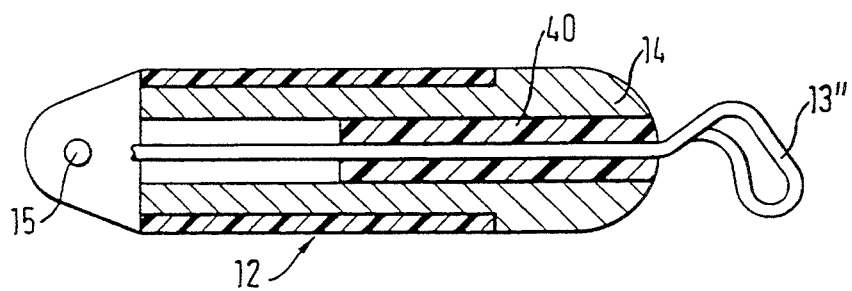
FIG. 10 shows a working tip provided with a cutting loop in a schematic, partly sectioned side view.

FIG. 10 shows a working tip 12 which is provided with a cutting loop 13" at its distal end. This cutting loop 13" does partially extend transversely to the central longitudinal axis of the working tip 12, but does not project radially over the working tip's outer perimeter, so that the cutting loop 13" does not inhibit the insertion of the instrument into a trocar and thus to the site of the operation. Nevertheless, the cutting loop 13" becomes viewable by the operator after it has been deployed about the axis of rotation 15, into the working position.

According to FIG. 11 and FIG. 11a, the working tip 12 has a coagulating electrode 13' with a forward convex end face 32 and a cutting needle 13. As in all the other embodiments, the neutral electrode 14 is formed in the manner of a tube and provided with a convex end face 33 at its distal end. A coaxial insulating layer 47 is between the neutral electrode 14 and the coagulating electrode 13', with the coagulating electrode being coaxial to the neutral electrode. The neutral electrode 14 is suitably likewise provided with an insulation 49 in the region behind the front end face 33.

Thus, in accordance with the invention, the centrally provided coagulating electrode 32 is forwardly moveable in the direction of the arrow in FIG. 11 into a coagulating position which is shown in FIG. 11a via an actuation mechanism 50 which is not shown in detail and only indicated in a broken manner in FIG. 11 and FIG. 11a. In the coagulating position, the front end faces 32, 33 form a continuous, approximately semi-spherical coagulating surface with the front end face of the insulating layer 47 which is disposed between the front end faces 32, 33. In this working position of the coagulating electrode 32, the cutting needle 13 which is provided coaxially in a bore 34 of the coagulating electrode 13' is pulled back in the direction of the arrow in FIG. 11 by an actuation mechanism 51 which is only indicated in a broken manner, such that the cutting needle 13 does not forwardly project over the front end face 32 of the coagulating electrode 13'.

The cutting needle 13 can however be forwardly pushed in the direction of the arrow in FIG. 11a into the position which is shown in FIG. 11 via an actuation mechanism 51, while simultaneously the coagulating electrode 13' is pulled back into the position which is shown in FIG. 11.

By pivotal connection of the working tip 12 which is shown in FIG. 11 and in FIG. 11a via the axis of rotation 15 to a tube shaft 11 featured in one of the preceding examples of the embodiment, an especially high degree of versatility can be attained. The working tip 12 can not only be angled by the above described pivoting from the axially aligned insertion position and withdrawal position into a working position, but optionally the coagulating electrode 13' or the cutting needle 13 can be made active or inactive in the way which is evident from FIG. 11 and FIG. 11a.

What is claimed is:

1. Bipolar radio-frequency surgical instrument comprising a rigid tube shaft having a longitudinal axis, a working tip having a longitudinal axis and substantially the same cross-section as an adjoining part of the tube shaft, the working tip being provided with at least one working electrode which can be energized with a radio-frequency voltage and a neutral electrode, means connecting the working tip with a front end of the rigid tube shaft so that the longitudinal axis of the working tip can be angularly moved about an axis transverse to the longitudinal axis of the tube shaft from a position in which it is axially aligned with the longitudinal axis to a position in which it is angularly inclined relative to the longitudinal axis, and a spring arranged eccentrically to the transverse axis and a diametrically oppositely disposed draw member for moving the working tip between the position in which its axis is angularly inclined and the position in which it is axially aligned with the longitudinal axis of the tube shaft.

2. Bipolar radio-frequency surgical instrument comprising a rigid tube shaft having a longitudinal axis, a working tip having a longitudinal axis and substantially the same cross-section as an adjoining part of the tube shaft, the working tip being provided with at least one working electrode which can be energized with a radio-frequency voltage and a neutral electrode, means connecting the working tip with a front end of the rigid tube shaft so that the longitudinal axis of the working tip can be angularly moved about an axis transverse to the longitudinal axis of the tube shaft from a position in which it is axially aligned witch the longitudinal axis to a position in which it is angularly inclined relative to the longitudinal axis, and a symmetrically arranged coil spring and a draw member for moving the working tip between the position in which its axis is angularly inclined and the position in which it is axially aligned with the axis of the tube shaft.

3. Bipolar radio-frequency surgical instrument comprising a rigid tube shaft having a longitudinal axis, a working tip having a longitudinal axis and substantially the same cross-section as an adjoining part of the tube shaft, the working tip being provided with at least one working electrode which can be energized with a radio-frequency voltage and a neutral electrode, means connecting the working tip with a front end of the rigid tube shaft so that the longitudinal axis of the working tip can be angularly moved about an axis transverse to the longitudinal axis of the tube shaft from a position in which it is axially aligned with the longitudinal axis to a position in which it is angularly inclined relative to the longitudinal axis, and a connecting element constructed of a resilient material between the tube shaft and the working tip and a draw member for moving the working tip between the position in which its axis is angularly inclined and the position in which it is axially aligned with the axis of the tube shaft.

4. Instrument in accordance with one of claims 1, 2 and 3 wherein the transverse axis between the tube shaft and the working tip is disposed less than 10 cm away from a front end of the working electrode.

5. Instrument in accordance with one of claims 1, 2 and 3 including a hinge attaching the working tip to the rigid tube shaft.

6. Instrument in accordance with one of claims 1 and 3 including at least one flexural spring element between the tube shaft and the working tip.

7. Instrument in accordance with claim 6 wherein the at least one flexural spring element is positioned eccentrically to the longitudinal axis of the tube shaft.

8. Instrument in accordance with claim 6 wherein the at least one flexural spring element has a section modulus which is at least three times as large in a plane of bending as in a plane perpendicular thereto.

9. Instrument in accordance with claim 6 wherein the at least one flexural spring element is formed as a leaf spring having a flat side facing towards the longitudinal axis of the tube shaft.

10. Instrument in accordance with claims 1, 2 and 3 wherein the spring is constructed of a material selected from the group consisting of spring steel, spring bronze and super-elastic Ni—Ti—alloy.

11. Instrument in accordance with one of claims 1, 2 and 3 wherein the working tip is formed as a bipolar cutting needle and including a large-area neutral electrode located immediately behind the bipolar cutting needle.

12. Instrument in accordance with one of claims 1, 2 and 3 wherein the working tip is formed as a combined bipolar cutting element and coagulating element.

13. Instrument in accordance with one of claims 1, 2 and 3 wherein the working tip forms an angle of at least 20° with the longitudinal axis of the rigid tube shaft when the working tip is in a position of maximum angular inclination relative to the longitudinal axis of the rigid tube shaft.

* * * * *

UNITED STATES PATENT AND TRADEMARK OFFICE
CERTIFICATE OF CORRECTION

PATENT NO. : 5,441,499
DATED : August 15, 1995
INVENTOR(S) : Gernod Fritzsch

It is certified that error appears in the above-indentified patent and that said Letters Patent is hereby corrected as shown below:

Title page, item [73] Assignee: change "Dekna" to --Delma--.

Signed and Sealed this

Second Day of January, 1996

Attest:

BRUCE LEHMAN

*Attesting Officer*      *Commissioner of Patents and Trademarks*